United States Patent [19]

Ameyama et al.

[11] Patent Number: 4,994,382

[45] Date of Patent: Feb. 19, 1991

[54] PROCESS FOR PRODUCTION OF PYRROLO-QUINOLINE QUINONE

[75] Inventors: Minoru Ameyama; Osao Adachi, both of Yamaguchi, Japan

[73] Assignee: Ube Industries, Ltd., Yamaguchi, Japan

[21] Appl. No.: 357,668

[22] Filed: May 26, 1989

Related U.S. Application Data

[63] Continuation of Ser. No. 739,046, May 29, 1985, abandoned.

[30] Foreign Application Priority Data

May 29, 1984 [JP] Japan ................................ 59-107406

[51] Int. Cl.$^5$ ..................... C12N 1/20; C12P 17/18; C12P 17/16; C12R 1/38
[52] U.S. Cl. ................................. 435/119; 435/118; 435/133; 435/247; 435/252.34; 435/253.3; 435/822; 435/874
[58] Field of Search ............... 435/119, 118, 133, 247, 435/822, 874, 253.3, 252.34

[56] References Cited

U.S. PATENT DOCUMENTS 4,317,843   3/1982   MacLennan et al. ................ 435/253

FOREIGN PATENT DOCUMENTS 206471   4/1986   European Pat. Off. ............ 435/118

OTHER PUBLICATIONS

Duine et al., "The Prosthetic Group of Methanol Dehydrogenase"; *Biochem. J.*, vol. 187, (1980), pp. 221–226.
Drieg et al., *Bergey's Manual of Systematic Bacteriology*, vol. 1, Williams and Wilkins, Baltimore, Md., (1984); pp. 399, 400.
Ameyama et al., "Microbial Production of Pyrrolo-Quinorine Quinone"; *Agric. Biol. Chem.*, vol. 48, No. 2, Feb. 1984, pp. 561–565.
Shimao et al., "Pyrroloquinoline Quinone as an Essential Growth Factor for a Poly(vinyl alchol)–Degrading Symbiont, *Pseudomonas* sp VM15C"; *Agric. Biol. Chem.*, vol. 48, No. 11, (Nov., 1984), pp. 2873–2876.
DeBeer et al.; "The Prosthetic Group of Methylamine Dehydrogenase From Pseudomonas AMI"; *Biochimica et Biophysica Acta*, vol. 622, (1980), pp. 370–374.
Chemical Abstracts, vol. 100, No. 21, (1984), p. 496, Abstract No. 173083r, Ameyama et al.
Chemical Abstracts, vol. 99, No 15, (1983), p. 287, Abstract No. 118240a, J. A. Duine et al.
Patent Abstracts of Japan, vol. 8, No. 323, (1984).
E. J. Corey et al., J. Am. Chem. Soc. 1981, 103, 5599–5600.

*Primary Examiner*—Herbert J. Lilling
*Attorney, Agent, or Firm*—Finnegan, Henderson, Farabow, Garrett & Dunner

[57] ABSTRACT

There are disclosed a new process for production of pyrrolo-quinoline quinone, comprising culturing a bacterium belonging to the genus Paracoccus, Protaminobacter or Pseudomonas and capable of producing pyrrolo-quinoline quinone in a culture medium to produce the pyrrolo-quinoline quinone in the cultured broth, and recovering the pyrrolo-quinoline quinone from the cultured broth; and a new process for production of pyrrolo-quinoline quinone, comprising culturing a bacterium belonging to the genus Paracoccus, Protaminobacter or Pseudomonas and capable of producing the pyrrolo-quinoline quinone in a culture medium to form cultured cells, separating the cells from the cultured broth, resuspending the separated cells in a reaction medium containing precursors of the pyrrolo-quinoline quinone, incubating the reaction medium to produce the pyrrolo-quinoline quinone, and recovering the pyrrolo-quinoline quinone from the reaction medium.

2 Claims, 2 Drawing Sheets

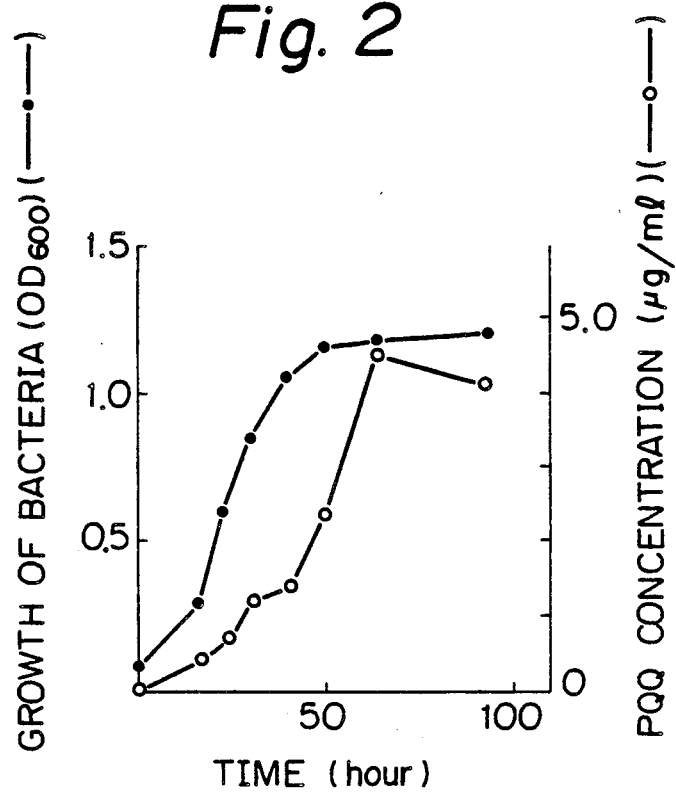

PROCESS FOR PRODUCTION OF PYRROLO-QUINOLINE QUINONE

This application is a continuation of application Ser. No. 06/739,046, filed May 29, 1985.

BACKGROUND OF THE INVENTION

1. Field of the Invention

The present invention relates to a process for the microbial production of pyrrolo-quinoline quinone (hereinafter referred to as PQQ).

2. Description of the Related Art

PQQ has the following formula:

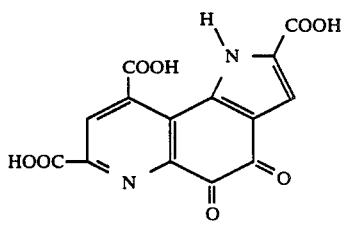

(I)

and can be reversibly reduced to a reduced type PQQ (PQQH$_2$) having the following formula:

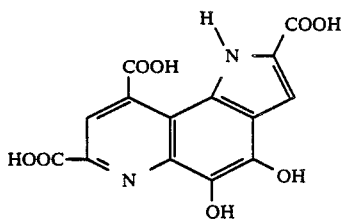

(II)

On the basis of this property, PQQ has an ability to convert apo-type quinoenzymes to the holo-type thereof. For example, PQQ acts as a coenzyme for methanol dehydrogenase in methanol-utilizing bacteria, alcohol dehydrogenase, aldehyde dehydrogenase, glycerol dehydrogenase, glucose dehydrogenase, or the like in acetic acid bacteria. PQQ is also physiologically important as a coenzyme for copper containing amine oxidase of animal, plant or microbial origin, amine dehydrogenase or choline dehydrogenase, or other various kinds of oxidoreductases which are inhibited by carbonyl reagents.

Moreover, PQQ may be a very important substance having vitamin actions because it acts as a coenzyme for important enzymes as described above, taking as an analogy the fact that coenzymes for other oxidoreductases and transferases, such as thiamine pyrophosphate, nicotinamide adenine dinucleotide, nicotinamide adenine dinucleotide phosphate, pyridoxal phosphate, flavin adenine dinucleotide, and flavin mononucleotide have to be taken in as vitamin, such as vitamin B$_1$, nicotinic acid, vitamin B$_6$, and vitamin B$_2$, respectively. On the basis of the above-mentioned physiological importance, PQQ is useful for pharmaceutical purposes.

Conventionally, for the production of PQQ, chemical synthetic processes are known (see, for example, *J. Am. Chem. Soc.* Vol. 103, 5599–5600 (1981)). However, these chemical synthetic processes have various disadvantages. For example, the processes are time-consuming due to the necessity for multi-reaction steps, require complicated operations to remove many kinds of by-product isomers derived from the reactions, and provide a rather low yield of PQQ.

To overcome the above-mentioned disadvantages of the chemical synthetic processes, there has been presented a biological process for the production of PQQ wherein cells of a microorganism are cultured in a medium to accumulate PQQ and related compounds, and the accumulated PQQ is recovered by, for example, extraction with solvents (see Japanese Unexamined Patent Application (Kokai) No. 59-113896 published on June 30, 1984), or simple chromatographic method on ionexchangers (see, for example, *Agri. Biol. Chem.* Vol 48, 561–565 (1984)).

Therefore, a new process for the production of PQQ, which is more practical and economical, is desired.

SUMMARY OF THE INVENTION

The present invention provides a new process for the production of PQQ comprising, culturing a bacterium belonging to the genus Paracoccus, Protaminobacter or Pseudomonas and capable of producing pyrrolo-quinoline quinone in a culture medium to produce the pyrrolo-quinoline quinone in the cultured broth, and recovering the pyrrolo-quinoline quinone from the cultured broth.

There is also provided a process for the production of PQQ comprising culturing the above-mentioned bacterium in a culture medium, to form cultured cells, separating the cells from the cultured broth, resuspending the separated cells in a reaction medium containing precursors of the pyrrolo-quinoline quinone, incubating the reaction medium to produce the pyrrolo-quinoline quinone, and recovering the pyrrolo-quinoline quinone from the reaction medium.

BRIEF DESCRIPTION OF THE DRAWINGS

FIG. 2 is a graph showing a profile of the culturing of *Paracoccus denitrificans* in Example 1.

DESCRIPTION OF THE PREFERRED EMBODIMENTS

Figure 1:
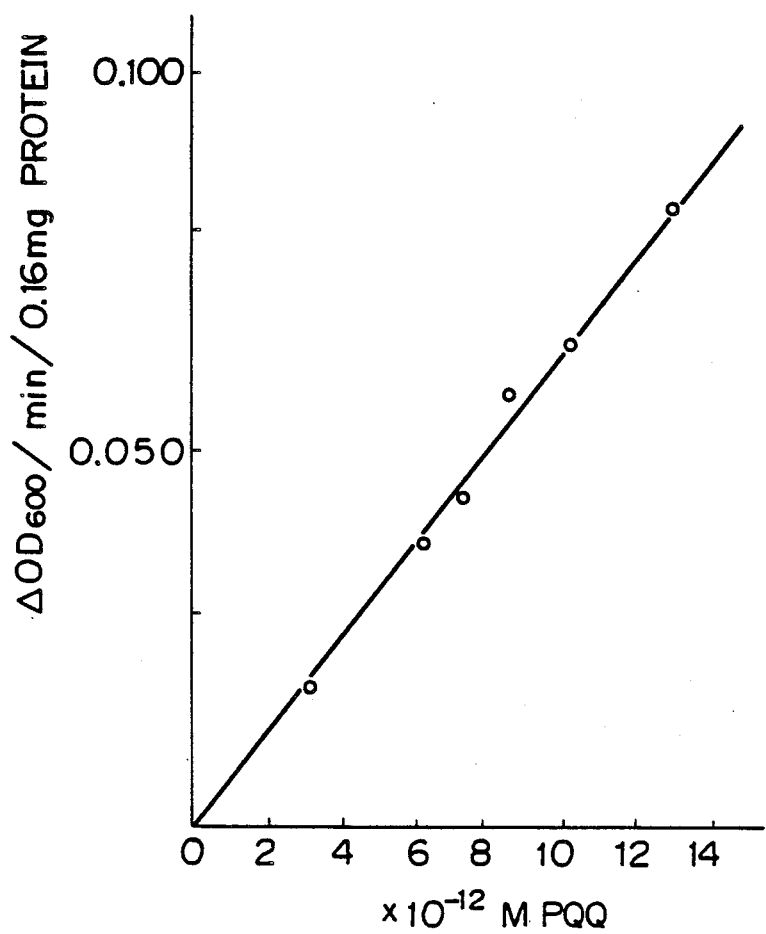
FIG. 1 is a calibration chart showing the relationship between an amount of PQQ and a difference of absorption per minute at 600 nm as measured by using a membrane of 0.16 mg as protein ($\Delta$OD600/min./0.16 mg).

The following bacteria are typically used in the present invention:

(1) *Paracoccus denitrificans* (IFO 13301)
(2) *Protaminobacter ruber* (IFO 3708)
(3) *Pseudomonas* A1-2 (FERM P-7599)
(4) *Pseudomonas* P1-1 (FERM P-7598)
(5) *Pseudomonas* P2-2 (FERM P-7600)
(6) *Pseudomonas* P2-3 (FERM P-7597)
(7) *Pseudomonas* N1-1 (FERM P-7596)

The above-mentioned bacteria (1) and (2) have been deposited at the Institute for Fermentation, Osaka (IFO) in Japan, and can be freely supplied to the public. The bacteria (3) to (7) were isolated by the present invention, and deposited at the Fermentation Research Institute (FRI) in Japan, on April 27, 1984. The bacterium(7) was transferred to the international deposition under the Budapest Treaty on the International Recognition of the Deposit of Microorganisms for the Purposes of Patent Procedure on Apr. 25, 1985, and given the number FERM BP-775.

The properties of the newly isolated bacteria are set forth in the following tables.

TABLE 1

Growth of Microorganisms on Various Carbon Sources

| Carbon Source | A1-2 | P1-1 | P2-2 | P2-3 | N1-1 |
|---|---|---|---|---|---|
| Methanol | ++ | + | ++ | + | ++ |
| Formaldehyde | ± | − | − | ± | − |
| Sodium formate | − | ± | ± | − | ± |
| Ethanol | + | ++* | + | + | ++* |
| Acetaldehyde | − | − | ± | + | ± |
| Sodium acetate | + | +* | +* | + | +* |
| Methylamine | + | + | ± | ± | + |
| D-Glucose | ++ | + | ++ | ++ | + |
| Glycerol | ++ | ++ | + | + | + |
| D-Fructose | ++ | + | + | + | + |
| Malate | + | − | ± | − | − |
| D-Mannitol | + | ++* | ++* | + | ++ |
| Lactose | ++* | + | ± | ++ | + |
| Saccharose | + | ++* | +* | ++ | + |
| D-Galactose | + | + | + | + | − |
| L-Arabinose | + | + | + | + | − |
| D-Xylose | + | − | − | + | + |
| Polypepton** | ++ | + | ? | ++ | ? |

*Production of fluorescent pigments
++ OD600: not less then 1.0
+ OD600: 0.2 to 0.99
± OD600: 0.1 to 0.2
− OD600: less than 0.1
**Trade name of peptone, Takeda Chemical Industries, Japan

TABLE 2

Taxononic Properties

| Property | A1-2 | P1-1 | P2-2 | P2-3 | N1-1 |
|---|---|---|---|---|---|
| Color | pink | pink | pink | white | pink |
| Mobility | + | + | + | + | + |
| Gram stain | − | − | − | − | − |
| Physiological properties | | | | | |
| Fluorescent pigment (Peptone medium) | − | + | + | − | + |
| Catalase | ++ | ++ | ++ | ++ | ++ |
| Oxidase | ++ | ++ | ++ | ++ | ++ |
| Urease | ++ | + | + | + | ++ |
| Nitrate reduction | − | + | + | + | − |
| Indole formation | − | − | − | − | − |
| H₂S | + | − | + | + | − |
| Optimum pH | 6.8–7.3 | 6.8–7.3 | 6.8–7.3 | 6.8–7.3 | 6.8–7.3 |
| Optimum temperature | 30° C. | 30° C. | 30° C. | 30° C. | 30° C. |

++ Strong
+ Weak
− Negative

As shown in the tables, all the microorganisms (1) are gram negative rod, (2) are motile, (3) have catalase, oxidase and urease activities, (4) do not form indole, (5) utilize methanol and ethanol, (6) have an optimum pH of 6.8 to 7.3, and (7) have an optimum temperature of 30° C. On the basis of the above-mentioned properties and according to the classification criteria described in Bergey's Manual of Determinative Bacteriology, eighth edition, these microorganisms are identified as methanolutilizable Pseudomonas bacteria. These bacteria are different from Pseudomonas already described, and therefore, are new strains.

In one embodiment of the present process, one of the above-mentioned bacteria capable of producing PQQ is cultured in a culture medium. The culture medium is preferably a liquid medium, and contains a carbon source and nitrogen source. The carbon source is, for example, methanol, methylamine, or other substrates from which C₁-compound can be generated biologically. The medium preferably contains methanol as the carbon source at a concentration of 0.1 to 5.0%, preferably 0.5 to 3.0% by weight. All of the methanol may be added to the medium before the start of culturing, or it may be added step by step or continuously during culturing. The nitrogen source includes organic nitrogen sources such as amino acids, nucleic acids, protein hydrolyzates, yeast extract, corn steep liquor, and inorganic nitrogen sources such as ammonium salts, ammonia water, gaseous ammonia, and nitrates. The above-mentioned nitrogen sources may be used alone or in combination. The concentration of nitrogen source varies according to the kind of nitrogen source used, and is preferably within 0.05% to 0.5% by weight.

The culturing is preferably carried out under the aerobic condition which is accomplished by aeration and agitation of the medium in a fermentor, or by shaking a culture flask containing the medium. The temperature for culturing is generally 0° C. to 40° C., preferably 20° C. to 35° C. The pH of the medium is generally 2 to 9, preferably 5.5 to 8.0. The culturing time is generally 20 to 150 hours, preferably 50 to 100 hours. In the present embodiment, PQQ is accumulated in the cultured broth.

In the second embodiment of the present process, one of the above-mentioned bacteria is cultured in a culture medium, and the cultured cells are separated from the cultured broth. The separated cells are then resuspended in a reaction medium in which PQQ is accumulated. The culture medium is preferably the same as the culture medium described in the first embodiment. The pH and temperature for culturing in the second embodiment are preferably the same as those used in the first embodiment. The culturing time is preferably 5 to 20 hours. The reaction medium contains precursors of PQQ, which comprise at least one carbon source, for example, alcohols such as methanol or ethanol, or sugars such as mannitol, fructose or glucose, and at least one amino acid such as glutamic acid, aspartic acid, alanine, ornithine, tyrosine, and 3,4-dihydroxyphenylalanine (DOPA). The concentration of the carbon source is preferably 0.5 to 3.0% by weight, and the concentration of the amino acid is preferably 0.05 to 0.5% by weight. The reaction medium can contain a buffer, such as a phosphate buffer, to maintain the pH within the preferable range. The pH and temperature for the reaction are preferably the same as those used for the culturing. The reaction is carried out under the aerobic condition which is accomplished by aeration and agitation of the reaction medium in a reaction vessel, or by shaking a reaction flask containing the reaction medium.

PQQ accumulated in the cultured broth in the first embodiment or in the reaction medium in the second embodiment is recovered by conventional processes such as ion exchange chromatography, gel filtration, solvent extraction, affinity chromatography, or a combination thereof.

The assaying of PQQ for coenzyme activity and the assay of a concentration of PQQ produced in the cultured broth or reaction medium, are carried out according to the following method. The method is carried out using an apoenzyme of quinoenzyme, which may be prepared from a mutant of *Pseudomonas aeruginosa* which lacks D-glucose dehydrogenase activity (see FEBS Letters, Vol. 130, 179–183, 1981). The mutant cannot produce PQQ, but will produce and accumulate apoenzyme of D-glucose dehydrogenase to a normal level in the cell membrane. When a fraction of the cell membrane prepared from the mutant is added with a sample comprising a cultured broth, reaction medium or cell extract containing PQQ, the apoenzyme is converted to holoenzyme, and D-glucose dehydrogenase activity is expressed. A calibration chart showing a relationship of a concentration of PQQ and the enzyme activity expressed is prepared within a range wherein the strength of the enzyme activity is proportional to the concentration of the PQQ, using standard chemically synthesized PQQ. An example of the calibration chart is shown in FIG. 1. The amount of PQQ in a sample is determined by comparing the strength of the enzyme activity measured for the sample with the calibration chart. The amount of PQQ may be also determined in the same manner as described above using an apoenzyme of any other quinoenzyme. Moreover, the amount of PQQ can be determined by a high performance liquid chromatography.

EXAMPLES

The present invention will now be further illustrated by, but is by no means limited to, the following examples.

EXAMPLE 1

To 100 ml of a culture medium containing 1% methanol, 0.2% $NaNO_3$, 0.2% $(NH_4)_2SO_4$, 0.1% $K_2HPO_4$, 0.02% $MgSO_4.7H_2O$, 0.00005% $H_3BO_3$, 0.000004% $CuSO_4.5H_2O$, 0.00002% $MnSO_4.H_2O$ 0.00002% $(NH_4)_2MoO_4$, 0.00004% $ZnSO_4.7H_2O$, 0.0015% $CoCl_2.2H_2O$, 0.004% KCl, and 0.0001% $FeSO_4.7H_2O$ (pH 7.0) in a 500 ml conical flask, cells of *Paracoccus denitrificans* (IFO 13301) are inoculated, and the flask shaken at 30° C. and 100 to 120 rpm.

FIG. 2 represents a profile of the culturing, wherein an amount of PQQ accumulated in the medium reaches to the maximum point during the period from the late logarithmic phase to the early stationary phase. In Table 2, the ordinate axis represents the change of absorption per minute, which represents a glucose dehydrogenase activity, in turn, represents an amount of PQQ in the medium.

To determine the amount of PQQ in the medium, a sample of the medium was obtained at any predetermined time, and centrifuged to obtain a supernatant. The supernatant (0.1 ml) was added to 33 micro grams of a cell membrane fraction containing apo-D-glucose dehydrogenase to obtain 0.11 ml of a mixture, and the mixture was incubated at 30° C. for 30 minutes to allow the conversion of the apo-D-glucose dehydrogegase to the holoenzyme. To the mixture, 1 ml of 50 mM tris(hydroxymethyl)aminomethane-HCl buffer, pH 8.75, containing 24 mM sodium azide, 0.04 ml of 6.7 mM 2,6-dichlorophenolindophenol, and 0.2 ml of 6 mM phenazine methosulfate are added, and topped-up with water to the total volume of 2.9 ml. A blank mixture was prepared by the same procedure. Absorbances at 600 nm of the sample mixture and the blank mixture were monitored at 25° C., and it was confirmed that there was no difference between the sample mixture and blank mixture. To the mixture, 0.1 ml of 1 M glucose solution containing 8 mM sodium azide was added, and after the addition, the change of the absorbance was recorded, and the change per minute was calculated. The added glucose was dehydrogenated by holo-D-glucose dehydrogenase, which has been formed from apo-D-glucose dehydrogenase and PQQ in the sample, and simultaneously, 2,4-dichlorophenolindophenol present in the reaction mixture was reduced, resulting in a fading of the blue color. Therefore, the extent of the fading, i.e., change of absorption at 600 nm, was correctly proportional to the amount of PQQ in the sample. The concentration of PQQ in the sample was obtained by comparing the change of absorbance with the calibration chart in FIG. 1, which was prepared using a chemically synthesized standard PQQ.

The growth of the microorganism was monitored by absorbance at 600 nm of the cultured medium.

When the concentration of PQQ in the cultured medium reached the maximum point, the culturing was terminated, and the cultured medium was removed and centrifuged to obtain a supernatant. The supernatant was applied on a DEAE Sephadex A-25 (Seikagaku Kogyo, Japan) column previously equilibrated with 0.002 M potassium phosphate, pH 7.0, and impurities were eluted with the same buffer containing 0.2 M KCl, and finally, fractions containing PQQ were eluted with the same buffer containing 0.6 M KCl.

The combined fraction containing PQQ was subjected to liquid chromatographic analysis under the following condition. The result of the analysis showed be the same retention time (13 minutes) for the fraction obtained as above, and for the chemically synthesized PQQ.

Apparatus: High Performance Liquid Chromatograph, Trirotor, Nippon Kogaku K.K., Japan
Column: HW-40S, Toyopearl
Eluent: Water-acetonitrile (1:1)
Detector: UV (254 nm)
Flow rate: 10 ml/min By repeating the above-mentioned chromatography, PQQ was isolated from the fraction, and 325 micrograms of PQQ were obtained.

EXAMPLES 2, 3, 4, 5, 6, and 7

Example 1 was repeated using the microorganisms set forth in Table 3, and PQQ accumulated in the cultured medium in the amount set forth in the same Table.

TABLE 3

| Example | Microorganism | | Culture time (hr.) | PQQ ($\mu$g/ml) |
|---|---|---|---|---|
| 2 | *Protaminobacter ruber* | (IFO3708) | 94 | 5.8 |
| 3 | *Pseudomonas* A1-2 | (FERM P-7599) | 45 | 4.9 |
| 4 | *Pseudomonas* P1-1 | (FERM P-7598) | 60 | 4.6 |
| 5 | *Pseudomonas* P2-2 | (FERM P-7600) | 50 | 14.5 |
| 6 | *Pseudomonas* P2-3 | (FERM P-7597) | 60 | 7.8 |
| 7 | *Pseudomonas* N1-1 | (FERM P-7596) | 50 | 26.1 |

EXAMPLE 8

30 l of a medium having the same composition as described in Example 1 was incorporated in a 50 l fermentor, and the medium was inoculated with an inoculam containing cells of Pseudomonas N1-1 (FERM P-7596), aerated at 30 l/min., and agitated at 500 rpm. A concentration of methanol in the medium was maintained at 1% by adding methanol during the culturing. The culturing was continued for 50 hours. The concentration of PQQ reached 30 $\mu$g/ml.

EXAMPLE 9

Example 1 was repeated except that the concentration of methanol was varied as described in Table 4. PQQ was produced in the concentration set forth in the same Table.

TABLE 4

| Concentration of methanol (%) | PQQ (μg/ml) |
| --- | --- |
| 0.1 | 0.5 |
| 0.25 | 1.8 |
| 0.5 | 2.0 |
| 1.0 | 4.5 |
| 3.0 | 3.6 |

EXAMPLE 10

*Protaminobacter ruber* (IFO 3708) was cultured in a medium having the same composition as in Example 1, for 50 hours. Cells were separated from the cultured medium, washed with distilled water, and resuspended in distilled water to a concentration of $OD_{600} = 10.0$. The suspension was then diluted with 0.1 M potassium phosphate buffer to a concentration of $OD_{600} = 1.0$, and methanol (final concentration 1.0%), and glutamic acid (final concentration 0.6%) were added to the diluted cell suspension. As a control, a diluted cell suspension containing no additives was prepared. These three suspensions were incubated at 30° C., and the concentration of PQQ produced in the reaction medium was determined as described in Example 1. The results are set forth in Table 5.

TABLE 5

| Additive | Concentration of PQQ (μg/ml) | |
| --- | --- | --- |
| | 6 hours | 15 hours |
| Methanol | 2.8 | 4.3 |
| Methanol + Glutamic acid | 4.8 | 3.8 |

TABLE 5-continued

| Additive | Concentration of PQQ (μg/ml) | |
| --- | --- | --- |
| | 6 hours | 15 hours |
| None | 0.2 | 0.6 |

Under the presence of both methanol and glutamic acid, production of PQQ was almost doubled in the 6 hours period.

We claim:

1. A process for producing pyrrolo-quinoline quinone, comprising culturing a bacterium Pseudomonas N1-1 (FERM BP-775) in a culture medium containing methanol at a concentration of from 0.5% to 5.0% by weight under conditions in which said bacterium can grow to produce said pyrrolo-quinoline quinone in the cultured medium, and recovering at least about 26.1 ug/ml of the pyrrolo-quinoline quinone from the cultured medium.

2. A process for producing pyrrolo-quinoline quinone, comprising culturing a bacterium Pesudomonas N1-1 (FERM BP-775) in a culture medium to form cultured cells, separating the cells from the cultured broth, resuspending the separated cells in a reaction medium comprising a carbon source at a concentration of from 0.5% to 3.0% by weight, wherein the carbon source is selected from the group consisting of methanol, ethanol, mannitol, fructose and glucose, and a nitrogen source at a concentration of from 0.05% to 0.5% by weight wherein the nitrogen source is selected from the group consisting of glutamic acid, aspartic acid, alanine, ornithine, tyrosine and 3,4-dihydroxyphenylalanine (DOPA), incubating the reaction medium to produce the pyrrolo-quinoline quinone, and recovering at least about 26.1 ug/ml of the pyrrolo-quinoline quinone from the reaction medium.

* * * * *